(12) United States Patent
Freeman et al.

(10) Patent No.: US 9,193,663 B2
(45) Date of Patent: Nov. 24, 2015

(54) METHODS FOR PRODUCING A VINYL ACETATE COMPOSITION HAVING A LOW IMPURITY CONTENT

(75) Inventors: Jessica Freeman, Pasadena, TX (US); Qiang Yao, Baton Rouge, LA (US); Lauren Moore, Webster, TX (US); Ilias Kotsianis, Houston, TX (US); Victor Johnston, Houston, TX (US); Kevin Hanks, League City, TX (US)

(73) Assignee: Celanese International Corporation, Irving, TX (US)

( * ) Notice: Subject to any disclaimer, the term of this patent is extended or adjusted under 35 U.S.C. 154(b) by 995 days.

(21) Appl. No.: 13/280,676

(22) Filed: Oct. 25, 2011

(65) Prior Publication Data

US 2012/0108842 A1    May 3, 2012

Related U.S. Application Data

(60) Provisional application No. 61/407,684, filed on Oct. 28, 2010.

(51) Int. Cl.
*C07C 67/60* (2006.01)
*C07C 67/62* (2006.01)

(52) U.S. Cl.
CPC ............... *C07C 67/60* (2013.01); *C07C 67/62* (2013.01)

(58) Field of Classification Search
CPC .......... C07C 67/60; C07C 67/62; C07C 69/15
USPC ...................................................... 560/261
See application file for complete search history.

(56) References Cited

U.S. PATENT DOCUMENTS

| | | | |
|---|---|---|---|
| 4,021,476 A | 5/1977 | Harbuck | |
| 4,156,632 A | 5/1979 | Roscher et al. | |
| 4,713,263 A * | 12/1987 | Lunsford et al. | 427/206 |
| 4,818,347 A | 4/1989 | Roscher et al. | |
| 5,001,259 A | 3/1991 | Smith et al. | |
| 5,185,308 A | 2/1993 | Bartley et al. | |
| 5,691,267 A | 11/1997 | Nicolau et al. | |
| 6,040,474 A | 3/2000 | Jobson et al. | |
| 6,114,571 A | 9/2000 | Abel et al. | |
| 6,228,226 B1 | 5/2001 | Hess et al. | |
| 6,476,261 B2 | 11/2002 | Ellis et al. | |
| 6,603,038 B1 | 8/2003 | Hagemeyer et al. | |
| 6,696,596 B1 | 2/2004 | Herzog et al. | |
| 6,852,877 B1 | 2/2005 | Zeyss et al. | |

FOREIGN PATENT DOCUMENTS

| | | |
|---|---|---|
| DE | 2945913 | 6/1981 |
| DE | 10042695 | 3/2002 |
| EP | 0330853 | 9/1989 |
| EP | 0672453 | 2/1995 |
| FR | 2343714 | 10/1977 |
| GB | 1248856 | 10/1971 |
| GB | 1559540 | 1/1980 |
| GB | 2160520 | 12/1985 |
| JP | 2006069916 | 3/2006 |
| JP | 2006232874 | 9/2006 |
| KR | 20080097529 | 11/2008 |
| WO | 2006/055183 A1 | 5/2006 |
| WO | WO 2007/045886 | 4/2007 |
| WO | WO 2010/149527 | 12/2010 |

OTHER PUBLICATIONS

Machine translation for JP 2006 069916.*
Shushunova et al. Vysokomolekulyarnye Soedineniya, Seriya A i Seriya, 2009, 51(12), 2135-2145.*
Chinese Office Action mailed on Jul. 2, 2014 for CN Patent Application No. 201180052412.4, with English translation, 11 pages.
Chinese Office Action mailed on Mar. 4, 2015 for CN Patent Application No. 201180052412.4, with English translation, 10 pages.
International Search Report and Written Opinion for PCT/US2011/057627 mailed Dec. 12, 2011 (18 pages).
International Preliminary Report on Patentability mailed Feb. 8, 2013 in corresponding International Application No. PCT/US2011/057627.

* cited by examiner

*Primary Examiner* — Yong Chu
*Assistant Examiner* — Ana Z Muresan (57) ABSTRACT

In one embodiment, the invention is to a method for producing a vinyl acetate composition. The method comprises the step of contacting acetic acid, oxygen, and ethylene under conditions effective to form a crude vinyl acetate composition comprising vinyl acetate, acetic acid, residual oxygen, and water. The method further comprises the step of contacting the crude vinyl acetate composition or a derivative thereof with at least one scavenger to form a treated crude vinyl acetate composition.

27 Claims, 2 Drawing Sheets

METHODS FOR PRODUCING A VINYL ACETATE COMPOSITION HAVING A LOW IMPURITY CONTENT

This application claims priority to U.S. Provisional Application No. 61/407,684, filed on Oct. 28, 2010, the entirety of which is incorporated herein by reference.

FIELD OF THE INVENTION

This invention relates to processes for producing vinyl acetate and, in particular, to improved processes for producing vinyl acetate, which processes reduce the amount vinyl acetate by-products in the vinyl acetate product.

BACKGROUND OF THE INVENTION

Vinyl acetate is an important monomer in the production of polyvinyl acetate and polyvinyl alcohol products. Vinyl acetate is conventionally prepared by contacting acetic acid and ethylene with molecular oxygen to form a crude vinyl acetate composition. The reaction is typically conducted in the presence of a suitable catalyst, which may comprise palladium, an alkali metal acetate promoter, and, optionally, a co-promoter, e.g., gold or cadmium, on a catalyst support. U.S. Pat. No. 6,696,596, for example, indicates that it is well known to manufacture vinyl acetate in a reaction in the gas phase with acetic acid and oxygen or oxygen containing gasses over fixed-bed catalysts. U.S. Pat. No. 6,040,474, as another example, describes the manufacture of acetic acid and/or vinyl acetate using two reaction zones wherein the first reaction zone comprises ethylene and/or ethane for oxidation to acetic acid with the second reaction zone comprising acetic acid and ethylene with the product streams being subsequently separated thereby producing vinyl acetate. Also, U.S. Pat. No. 6,476,261 describes an oxidation process for the production of alkenes and carboxylic acids such as ethylene and acetic acid, which are reacted to form vinyl acetate, demonstrating that more than one reaction zone can be used to form the vinyl acetate.

This vinyl acetate reaction, however, lends itself to the production of several unwanted impurities, including, for example, non-volatile residues such as polymerized vinyl acetate, polymerized ethylene, and heavy ends, such as acetoxyacetic acid. The formation of these by-products is detrimental in many respects. For example, the formation of these by-products reduces vinyl acetate yield and may lead to fouling of vinyl acetate production equipment, e.g., purification towers and vaporizers.

Conventionally, a heavy ends tower is utilized to remove these by-products. The heavy ends tower, however, is expensive. Also, the level of purification achieved by the heavy ends tower leaves much to be desired. Thus, the need exists for methods for producing a vinyl acetate composition wherein the formation of impurities is inhibited or wherein the impurity content is reduced.

The disclosures of all of the references mentioned above are hereby incorporated by reference.

SUMMARY OF THE INVENTION

The present invention, in one embodiment, is to a method for producing a vinyl acetate composition. The method comprises the step of contacting acetic acid, oxygen, and ethylene under conditions effective to form a crude vinyl acetate composition. The crude vinyl acetate composition, as formed, comprises vinyl acetate, residual acetic acid, residual oxygen, water, and, optionally, residual ethylene and an initial amount of impurities, e.g., peroxides, NVR, heavy ends, and/or mixtures thereof. In one embodiment, the composition comprises one or more impurities in an amount ranging from 10 wppm to 15,000 wppm impurities, e.g., from 100 wppm to 10,000 wppm, or from 500 wppm to 5,000 wppm. The method further comprises the step of contacting the crude vinyl acetate composition or a derivative thereof with at least one scavenger, e.g., at least two or at least three, to inhibit formation of the one or more impurities. The contacting yields a treated crude vinyl acetate composition. The method may further comprise the step of purifying the treated crude vinyl acetate composition in a purification system to produce a purified vinyl acetate composition. In one embodiment, the contacting may be performed prior to the purification step.

In another embodiment, the invention is to a method for inhibiting the formation of impurities in an initial crude vinyl acetate composition comprising vinyl acetate, acetic acid, oxygen, and water. The method comprises the step of contacting the initial crude vinyl acetate composition or a derivative thereof with at least one scavenger to form a treated crude vinyl acetate composition. After contacting the initial crude vinyl acetate composition with the at least one scavenger, the treated crude vinyl acetate composition preferably comprises less than 2,000 wppm impurities, e.g., less than 1,000 wppm, less than 500 wppm, less than 250 wppm or less than 100 wppm.

In another embodiment, the invention is to a method for reducing existing peroxide content in an initial crude vinyl acetate composition. The initial crude vinyl acetate composition comprises vinyl acetate, an initial amount of peroxides, and optionally acetic acid and water. The method comprises the step of contacting the initial crude vinyl acetate composition or a derivative thereof with at least one scavenger to form a treated crude vinyl acetate composition. The treated crude vinyl acetate composition comprises vinyl acetate and a reduced amount of impurities. In one embodiment, the reduced amount of impurities is less than the initial amount, e.g., at least 10% less than the initial amount.

BRIEF DESCRIPTION OF DRAWINGS

The invention is described in detail below with reference to the appended drawings, wherein like numerals designate similar parts.

DETAILED DESCRIPTION OF THE INVENTION

Introduction

Conventional vinyl acetate processes suffer from the production of unwanted impurities such as non-volatile residues and heavy ends, which reduce yield and have detrimental effects on production equipment. Examples of affected production equipment include purification towers and vaporizers. As a result, significant resources must be devoted to remove these impurities from the crude vinyl acetate composition.

The present invention relates to the inhibition of the formation of vinyl acetate impurities and/or to the reduction of vinyl acetate impurity content in a vinyl acetate composition.

It has now been discovered that a significant amount of oxygen may be present in a vinyl acetate separation train, e.g., in a pre-dehydration column ("PDC"). It has also been discovered that one or more peroxides may form in a vinyl acetate reactor, in the resulting effluent stream that exits the reactor, as well as in the purification units associated with the reactor. Without being bound by theory, it is believed that polymerization of monomers may be induced by the presence of radicals, e.g., oxygen radicals. These oxygen radicals may be formed via the decomposition of oxygen and/or oxygen-containing compounds, e.g., peroxides. Thus, the oxygen and/or the peroxides, e.g. the oxygen and/or the peroxides in and around the reactor and the PDC, may give rise to the formation of many undesired impurities. For example, unwanted non-volatile residues ("NVR") are formed via the polymerization of monomers such as ethylene and vinyl acetate. As another example, the oxygen and/or the peroxides may promote the formation of undesirable heavy ends. Exemplary heavy ends include ethylene glycol, ethylidene diacetate, ethylene glycol monoacetate, vinyl acetoxy acetate, ethylene glycol diacetate, cis-diacetoxy ethylene, trans-diacetoxy ethylene, glycolic acid, acetoxyacetic acid, and mixtures thereof.

In view of these discoveries, the present invention, in some embodiments, is to a method for producing a vinyl acetate composition. The method comprises the step of contacting acetic acid, oxygen (pure or in a mixture, e.g., air), and ethylene under conditions effective to form a crude vinyl acetate composition. As an example, the vinyl acetate formation reaction may take place in a reactor and the crude vinyl acetate composition may comprise the reactor effluent stream. The crude vinyl acetate composition, as formed, comprises vinyl acetate, (residual) acetic acid, (residual) oxygen, water, and, optionally, residual ethylene and an initial amount of impurities, e.g., NVR, heavy ends, peroxides, and/or mixtures thereof. In one embodiment, the composition comprises one or more impurities. In one embodiment, the crude vinyl acetate composition comprises at least 5 wt. % vinyl acetate, e.g., at least 10 wt. %, at least 15 wt. %, or at least 20 wt. %; and at least 10 wppm impurities, e.g., at least 100 wppm, at least 500 wppm, at least 1,000 wppm, or at least 2,000 wppm. In terms of ranges, the crude vinyl acetate composition optionally comprises from 1 wt. % to 75 wt. % vinyl acetate, e.g., from 1 wt. % to 50 wt. %, from 2 wt. % to 35 wt. %, or from 5 wt. % to 15 wt. %; and from 10 wppm to 15,000 wppm impurities, e.g., from 100 wppm to 10,000 wppm, or from 500 wppm to 5,000 wppm. In terms of upper limits, the crude vinyl acetate composition optionally comprises less than 15,000 wppm impurities, e.g., less than 10,000 or less than 5,000.

In one embodiment where the impurities comprise peroxides, the crude vinyl acetate composition comprises at least 5 wppm peroxides, e.g., at least 10 wppm, at least 20 wppm or at least 25 wppm. In terms of ranges, the crude vinyl acetate composition may comprise from 5 wppm to 25 wppm peroxides, e.g., from 5 wppm to 20 wppm, from 5 wppm to 11 wppm, or from 10 wppm to 20 wppm. In another embodiment, the crude vinyl acetate composition may comprise, less than 50 wppm peroxides, e.g., less than 25 wppm, less than 15 wppm, or less than 11 wppm, as determined by potassium iodide UV-Vis method. Generally speaking, in the UV-V is method, peroxides are rapidly reacted with KI, according to the equation $$KI_{(s)} + H_2O_2 \rightarrow I_2 + 2KOH$$

to produce $I_2$, which is a colored species. The $I_2$ has a concentration directly correlated to the amount of peroxides in solution. This $I_2$ concentration may be quantified by producing a calibration curve with the absorbance at a particular wavelength. In another embodiment where the impurities comprise NVR and/or heavy ends, the crude vinyl acetate composition comprises at least 10 wppm impurities, e.g., at least 100 wppm, at least 500 wppm, at least 1,000 wppm, or at least 2,000 wppm. In terms of ranges, the crude vinyl acetate composition may comprise from 10 wppm to 15,000 wppm NVR and/or heavy ends, e.g., from 100 wppm to 10,000 wppm, or from 500 wppm to 5,000 wppm. In another embodiment, the crude vinyl acetate composition may comprise less than 15,000 wppm impurities, e.g., less than 10,000 or less than 5,000.

In preferred embodiments, the method further comprises the step of contacting the crude vinyl acetate composition or a derivative thereof with at least one scavenger, e.g., at least two or at least three, to inhibit formation of one or more impurities. A treated crude vinyl acetate composition is yielded as a result of the contacting. Preferably the treated crude vinyl acetate composition comprises a low amount of impurities.

In one embodiment, the derivative of the crude vinyl acetate composition comprises a stream that is yielded via a separation zone that separates the crude vinyl acetate composition. For example, the separation zone may comprise a first column, e.g. a PDC, which yields a distillate and a residue. Preferably, the crude vinyl acetate composition derivative comprises the distillate from the PDC. In other embodiments, the separation zone further comprises a second column, e.g., an azeotrope column, which separates the distillate from the first column (and/or a residue from the first column) into a distillate and a residue. In these cases, the crude vinyl acetate composition derivative preferably comprises the distillate from the second column. Of course, these are merely examples of crude acetic acid composition derivative streams and this listing is not exclusive. Some additional crude vinyl acetate derivative streams are discussed below.

As used herein, the singular term "scavenger," in some embodiments, means a plurality of scavengers or at least one scavenger, e.g., at least two or at least three.

In the formation of vinyl acetate, an acetic acid stream, an ethylene stream, and an oxygen stream are directed to a reactor (together or separately), and a crude vinyl acetate composition is yielded from the reactor. The method may further comprise the step of separating the crude vinyl acetate composition in a separation zone to produce a purified vinyl acetate composition. As one example, the contacting may be performed prior to the separation step. The scavenger, for example, may be added to the crude vinyl acetate composition as the effluent stream exits the reactor.

Without being bound by theory, it is believed that impurities, e.g., peroxides, are formed by equilibrium reactions between oxygen and various hydrogen sources present in and around the reactor. By contacting the effluent stream with the one or more scavengers prior to separation, these equilibrium reactions are inhibited resulting in less peroxide formation. When peroxide formation is thus inhibited, the formation of oxygen radicals may also be also inhibited. In other embodiments, the addition of scavengers to streams in high oxygen environments in and around the PDC, also inhibits the formation of oxygen radicals in these locations. As such, the formation of impurities that are promoted by these oxygen radicals, e.g., polymers of ethylene and/or vinyl acetate, may be inhibited as well. As such, the separation train associated with purifying the crude vinyl acetate may be simplified resulting in improved production efficiency. Also, the contacting of one or more of these streams with the scavenger inhibits impurity formation in the product mixture and/or, if impurities have already been formed, reduces impurity content. In this manner, the method improves vinyl acetate yield and reduces the problems associated with impurities in the purification equipment.

The invention, in another embodiment, is to a method for inhibiting the formation of impurities in an initial crude vinyl acetate composition comprising vinyl acetate, acetic acid, oxygen, and water. The method comprises the step of contacting the initial crude vinyl acetate composition or a derivative thereof with at least one scavenger to form a treated crude vinyl acetate composition. As a result of the contacting, the formation of impurities in the vinyl acetate product is inhibited. After contacting the initial crude vinyl acetate composition with the at least one scavenger, the treated crude vinyl acetate composition preferably comprises less than 2,000 wppm impurities, e.g., less than 1,000 wppm, less than 500 wppm, less than 250 wppm or less than 100 wppm. In terms of ranges, the treated crude vinyl acetate composition may comprise from 0 wppm to 2,000 wppm impurities, e.g., from 100 wppm to 1,000 wppm or from 250 wppm to 1,000 wppm. In another embodiment, the inhibited amount of impurities is less than the amount of impurities that would be present had the crude vinyl acetate composition not been contacted with the scavenger, e.g., at least 10% less than, at least 25% less than, or at least 40% less than.

In embodiments where the impurities comprise peroxides, the treated crude vinyl acetate composition comprises less than 10 wppm peroxides, e.g., less than 8 wppm or less than 7 wppm. In terms of ranges, the treated crude vinyl acetate composition may comprise from 0 wppm to 10 wppm peroxides, e.g., from 1 wppm to 8 wppm, or from 2 wppm to 7 wppm. In another embodiment, the inhibited amount of peroxides is less than the amount of peroxides that would be present had the crude vinyl acetate composition not been contacted with the scavenger, e.g., at least 10% less than, at least 25% less than, or at least 40% less than. In addition, in the event that the initial crude vinyl acetate composition comprises peroxides, the contacting preferably results in reducing the peroxide content. In another embodiment, the treated crude vinyl acetate composition comprises less peroxides than the initial crude vinyl acetate composition, e.g., at least 10% less peroxides, at least 25% less peroxides, or at least 40% less peroxides.

In embodiments where the impurities comprise NVR and/or heavy ends, the treated crude vinyl acetate composition comprises less than 2,000 wppm NVR and/or heavy ends, e.g., less than 1,000 wppm, less than 500 wppm, less than 250 wppm or less than 100 wppm. In terms of ranges, the treated crude vinyl acetate composition may comprise from 0 wppm to 2,000 wppm NVR and/or heavy ends, e.g., from 100 wppm to 1,000 wppm or from 250 wppm to 1,000 wppm. In another embodiment, the inhibited amount of NVR and/or heavy ends is less than the amount of NVR and/or heavy ends that would be present had the crude vinyl acetate composition not been contacted with the scavenger, e.g., at least 10% less than, at least 25% less than, or at least 40% less than. In addition, in the event that the initial crude vinyl acetate composition comprises NVR and/or heavy ends, the contacting preferably results in reducing the NVR and/or heavy ends content. In another embodiment, the treated crude vinyl acetate composition comprises less NVR and/or heavy ends than the initial crude vinyl acetate composition, e.g., at least 10% less, at least 25% less, or at least 40% less.

In an additional embodiment, the invention is to a method for reducing existing impurity content in an initial crude vinyl acetate composition. The initial crude vinyl acetate composition comprises vinyl acetate, an initial amount of impurities, and optionally acetic acid and water. The method comprises the step of contacting the initial crude vinyl acetate composition or a derivative thereof with at least one scavenger to form a treated crude vinyl acetate composition. The treated crude vinyl acetate composition comprises vinyl acetate and a reduced amount of impurities. In one embodiment, the reduced amount of impurities is less than the initial amount, e.g., at least 10% less than the initial amount, at least 25% less than the initial amount, or at least 40% less than the initial amount.

The scavenger(s) may vary widely. For example, in some embodiments, the scavenger may be selected from the group consisting of ascorbic acid, thiols, polyphenols, hydroquinone, 4-hydroxy-TEMPO, methyl hydroquinone, 2,2-biphenol, 4,4'-dihydroxybiphenol, 2,5-di-tert-butylhydroquinone, 2,6-di-tert-butyl-4-methylphenol, 4-methoxyphenol, (butylated) hydroxyanisole, nitrosobenzene, resorcinol, tert-butyl hydroquinone, tert-butylhydroquinone, 2-tert-butyl-4-methylphenol, 1,2,4-benzenetriol, N,N'-di-2-butyl-1,4-phenylenediamine, 2,4-dimethyl-6-tert-butylphenol, 2,6-di-tertbutylphenol, substituted alkylamines, parabenzoquinone, butylated hydroxytoluene, diphenyl picryl hydrazyl, and mixtures thereof. In one embodiment, the one or more scavenger is an antioxidant, an inhibitor, or a mixture thereof. In some cases, however, a scavenger may have both antioxidant properties and inhibitor properties and the "antioxidant" or "inhibitor" nomenclature should not be considered as limiting.

In other embodiments, the at least one scavenger comprises a combination of scavengers. For example, the at least one scavenger may comprise an antioxidant and an inhibitor. In one embodiment, the contacting step comprises contacting the crude vinyl acetate composition with the antioxidant and the inhibitor. As one example, the inhibitor(s) may be combined with the antioxidant(s) to form a scavenger package and the scavenger package may contact the crude vinyl acetate composition. In other embodiments, the contacting step may include contacting the crude vinyl acetate composition with a first scavenger, e.g., an antioxidant, and a second scavenger, e.g., an inhibitor, separately. The scavenger package, in some embodiments, may contact the crude vinyl acetate composition to inhibit impurity formation, e.g., peroxide formation, NVR formation, or heavy ends formation. Preferred scavenger packages comprise substituted alkylamine and hydroquinone; parabenzoquinone and ascorbic acid; and parabenzoquinone and substituted alkylamine. In one embodiment, the scavenger package comprises additional additives that are known in the art, e.g., dispersants, such as oxyalkylated alkyl alcohol. In one embodiment, the scavenger package comprises a substituted alkylamine and an oxyalkylated alkyl alcohol.

Where the one or more scavenger are added to the initial crude vinyl acetate composition, the one or more scavenger may be present in an amount ranging from 1 wppm to 2,000 wppm, e.g., from 10 wppm to 1,500 wppm, or from 25 wppm to 500 wppm. In terms of lower limits, the scavenger may be present in amounts greater than 10 wppm, e.g., greater than 25 wppm, greater than 50 wppm, or greater than 100 wppm. In other embodiments, the scavenger may be present in amounts less than 2000 wppm, e.g., less than 1100 wppm, or less than 100 wppm.

In embodiments where the scavenger is used to inhibit peroxide formation, the one or more scavenger may be added to the initial crude vinyl acetate composition in an amount ranging from 10 wppm to 2,000 wppm, e.g., from 10 wppm to 1,100 wppm, or from 25 wppm to 100 wppm. In terms of lower limits, the scavenger may be present in amounts greater than 10 wppm, e.g., greater than 25 wppm, greater than 50 wppm, or greater than 100 wppm. In other embodiments, the scavenger may be present in amounts less than 2000 wppm, e.g., less than 1100 wppm, or less than 100 wppm.

By contacting the vinyl acetate composition with the at least one scavenger as discussed above, side reactions that form the peroxides are advantageously inhibited. This inhibition beneficially results in less peroxides (and subsequently less oxygen radicals) being formed. The formation of oxygen radicals in the high oxygen environments in and around the PDC, advantageously, is also inhibited. Thus, less oxygen radicals are present, which reduces impurity formation. Preferably, fewer impurities are formed in the crude vinyl acetate composition as it exits the reactor and/or as it is conveyed through the PDC. Because fewer impurities are formed in these areas, the need for removal of these impurities in the separation train is reduced and production efficiencies are improved.

Vinyl Acetate Formation

The features of the present invention may be applied to any suitable vinyl acetate production process. As noted above, the formation of vinyl acetate may be carried out by reacting acetic acid and ethylene in the presence of oxygen. In other embodiments, the inventive use of the scavengers may apply to production of other monomers such as, for example, acrylic acid, vinyl esters, or diacetoxyethylene. This reaction may take place heterogeneously with the reactants being present in the gas phase. The reactor may be configured such that the reactor is capable of removing heat from the reaction. Suitable reactor types include, but are not limited to, a fixed bed reactor and a fluidized bed reactor. Preferably, the molar ratio of ethylene to acetic acid in the reaction ranges from 1:1 to 10:1, e.g., from 1:1 to 5:1; or from 2:1 to 3:1. In one embodiment, the molar ratio of ethylene to oxygen in the reaction ranges from 1:1 to 20:1, e.g., from 1.5:1 to 10:1; or from 2:1 to 5:1. In another embodiment, the molar ratio of acetic acid to oxygen in the reaction ranges from 1:1 to 10:1, e.g., from 1:1 to 5:1; or from 1:1 to 3:1.

The acetic acid may be produced by any suitable method. As one example, the acetic acid may be produced via methanol carbonylation with carbon dioxide. Water may be formed in situ in a liquid reaction composition, for example, by the esterification reaction between the methanol reactant and the acetic acid product. In one embodiment, water is introduced to the carbonylation reactor together with or separately from other components of the liquid reaction composition. Water may be separated from other components of reaction composition, withdrawn from the reactor, and may be recycled in controlled amounts to maintain the required concentration of water in the liquid reaction composition. Preferably, the concentration of water maintained in the liquid reaction composition is in the range of from 0.1 wt. % to 16 wt. %, e.g., from 1 wt. % to 14 wt. %, or from 1 wt. % to 10 wt. %.

In another embodiment, the carbonylation reaction is a low water carbonylation, wherein the concentration of water maintained in the liquid reaction composition ranges from 0.1 wt. % to 14 wt. %, e.g., from 1 wt. % to 10 wt. %. The low water carbonylation may be conducted by maintaining in the reaction medium an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The disclosure of U.S. Pat. No. 5,001,259 is hereby incorporated by reference. The concentration of iodide ion maintained in the reaction medium of the preferred carbonylation reaction system is believed to be quite high as compared with what little prior art there is dealing with the use of halide salts in reaction systems of this sort. The absolute concentration of iodide ion content is not a limitation on the usefulness of the present invention.

The ethylene similarly may be produced by any suitable method. In one embodiment, the ethylene is formed via the hydrogenation of acetic acid followed by the dehydration of the acetic acid to form ethylene. As another alternative, the acetic acid and the ethylene may be produced via oxidation of an alkane, e.g., ethane, as discussed in U.S. Pat. No. 6,476,261, the disclosure of which is hereby incorporated by reference. The oxygen used in the formation of vinyl acetate in the method of the present invention may further comprise other inert gases such as nitrogen. As one example, the oxygen used in the vinyl acetate reaction is provided by an air stream.

In one embodiment, additional ethylene may be fed to the reactor. This additional ethylene, as well as the reactant ethylene mentioned above, may be substantially pure. In one embodiment, the ethylene may be admixed, for example, with one or more of nitrogen, methane, carbon dioxide, carbon monoxide, hydrogen, and low levels of $C_3/C_4$ alkenes/alkanes. Additional oxygen may be fed to the reactor. The additional oxygen, if used, may be air or a gas richer or poorer in molecular oxygen than air. One suitable additional molecular oxygen-containing gas may be, oxygen diluted with a suitable diluent, for example nitrogen or carbon dioxide. Preferably, the additional molecular oxygen-containing gas is oxygen. Preferably, at least some of the oxygen is fed to the reactor independently from the ethylene and acetic acid.

The vinyl acetate reaction may suitably be carried out at a temperature in the range of from 100° C. to 300° C., e.g., from 140° C. to 220° C. or from 150° C. to 200° C. In another embodiment, the reaction may be carried out pressure in the range of from 0.1 MPa to 10 MPa, e.g., from 0.1 MPa to 2.5 MPa or from 1 MPa to 2.5 MPa.

Preferably, the reaction is conducted over a catalyst. Suitable catalysts include catalysts comprising a first metal and optionally one or more of a second metal, a third metal, or additional metals. The catalyst optionally comprises a catalyst support. The first and optional second and third metals may be selected from palladium, gold, boron, alkali metals, and Group IB or VIIIB transition metals. Preferred metal combinations include palladium/gold and palladium/boron.

The first metal optionally is present in an amount from 0.1 to 10 wt. %, e.g., from 0.2 to 5 wt. %, or from 0.2 to 2.5 wt. %. The additional metals, if present, may be present in amounts ranging from 0.1 to 10 wt. %, e.g., from 0.2 to 5 wt. %, or from 0.2 to 2.5 wt. %. In other embodiments, the catalyst may comprise metalloids, e.g., boron, in amounts ranging from 0.01 wt. % to 1 wt. %, e.g., from 0.01 wt. % to 0.2 wt. %. For catalysts comprising two or more metals, the two or more metals may be alloyed with one another. Alternatively, the two or more metals may comprise a non-alloyed metal solution or mixture. Also, the preferred metal ratios may vary depending on the metals used in the catalyst. If palladium and gold are utilized, the ratio may range from 0.5:1 to 20:1, e.g., from 1.8:1 to 10:1. In some exemplary embodiments where a first and second metal are used, the mole ratio of the first metal to the second metal is from 5:1 to 1:1, e.g., from 3:1 to 1:1, or from 2:1 to 1:1.

In addition to one or more metals, the exemplary catalysts further comprise a support or a modified support, meaning a support that includes a support material and a support modifier, which adjusts the acidity of the support material. The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that use a modified support, the support modifier is present in an amount from 0.1 wt. % to 50 wt. %, e.g., from 0.2 wt. % to 25 wt. %, from 0.5 wt. % to 15 wt. %, from 1 wt. % to 8 wt. %, from 1 wt. % to 5 wt. %, or from 2 wt. % to 4 wt. %, based on the total weight of the catalyst.

Suitable support materials may include silica, alumina, silica-alumina, titania, ticano-silicates, zirconia, zircono-silicate, niobia, silicates, alumino-silicates, titanates, carbon, metals, and glasses. Preferred supports include zirconia, zircono-silicates, and titano-silicates. Suitable support modifiers may include barium, magnesium, cerium, potassium, calcium, niobium, tantalum, titanium, yttrium, strontium, zirconium, vanadium, molybdenum, and rubidium. Preferred support modifiers include niobium, titanium, magnesium, and zirconium.

Specific examples of suitable catalysts include, for example, those described in GB 1 559 5401; EP 0 330 853; EP 0 672 4563; U.S. Pat. Nos. 5,185,308; 5,691,267; 6,114,571; 6,852,877; and 6,603,038. The disclosures of all of the above-mentioned references are hereby incorporated by reference.

GB 1 559 540 describes suitable catalysts that can be employed in the preparation of vinyl acetate by the reaction of ethylene, acetic acid and oxygen. The catalysts are comprised of: (1) a catalyst support having a particle diameter of from 3 to 7 mm and a pore volume of from about 0.2 to 1.5 ml per gram, a 10% by weight water suspension of the catalyst support having a pH from about 3.0 to 9.0, (2) a palladium-gold alloy distributed in a surface layer of the catalyst support, the surface layer extending less than 0.5 mm from the surface of the support, the palladium in the alloy being present in an amount of from about 1.5 to 5.0 grams per liter of catalyst, and the gold being present in an amount of from about 0.5 to 2.25 grams per liter of catalyst, and (3) from 5 to 60 grams per liter of catalyst of alkali metal acetate.

U.S. Pat. No. 5,185,308 describes a shell impregnated catalyst active for the production of vinyl acetate from ethylene, acetic acid, and an oxygen-containing gas, the catalyst consisting essentially of (1) a catalyst support having a particle diameter from about 3 to about 7 mm and a pore volume of 0.2 to 1.5 ml per gram, (2) palladium and gold distributed in the outermost 1.0 mm thick layer of the catalyst support particles, and (3) from about 3.5 to about 9.5% by weight of potassium acetate wherein the gold to palladium weight ratio in said catalyst is in the range 0.6 to 1.25.

U.S. Pat. No. 5,691,267 describes a two step gold addition method for a catalyst used in the gas phase formation of vinyl acetate from the reaction of ethylene, oxygen, and acetic acid. The catalyst is formed by (1) impregnating a catalyst carrier with aqueous solutions of a water-soluble palladium salt and a first amount of a water-soluble gold compound such as sodium-palladium chloride and auric chloride, (2) fixing the precious metals on the carrier by precipitating the water-insoluble palladium and gold compounds by treatment of the impregnated carriers with a reactive basic solution such as aqueous sodium hydroxide which reacts with the palladium and gold compounds to form hydroxides of palladium and gold on the carrier surface, (3) washing with water to remove the chloride ion (or other anion), and (4) reducing all the precious metal hydroxides to free palladium and gold, wherein the improvement comprises (5) impregnating the carrier with a second amount of a water-soluble gold compound subsequent to fixing a first amount of water-soluble gold agent, and (6) fixing the second amount of a water-soluble gold compound.

U.S. Pat. No. 6,114,571 describes a catalyst for forming vinyl acetate in the gas phase from ethylene, acetic acid, and oxygen or oxygen-containing gases wherein the catalyst is comprised of palladium, gold, boron, and alkali metal compounds on a support. The catalyst is prepared by a) impregnating the support with soluble palladium and gold compounds; b) converting the soluble palladium and gold compounds on the support into insoluble compounds by means of an alkaline solution; c) reducing the insoluble palladium and gold compounds on the support by means of a reducing agent in the liquid phase; d) washing and subsequently drying the support; e) impregnating the support with a soluble alkali metal compound; and f) finally drying the support at a maximum of 1500° C., wherein boron or boron compounds are applied to the catalyst prior to the final drying.

U.S. Pat. No. 6,603,038 describes a method for producing catalysts containing metal nanoparticles on a porous support, especially for gas phase oxidation of ethylene and acetic acid to form vinyl acetate. The invention relates to a method for producing a catalyst containing one or several metals from the group of metals comprising the sub-groups Ib and VIIIb of the periodic table on porous support particles, characterized by a first step in which one or several precursors from the group of compounds of metals from sub-groups Ib and VIIIb of the periodic table is or are applied to a porous support, and a second step in which the porous, preferably nanoporous support to which at least one precursor has been applied is treated with at least one reduction agent, to obtain the metal nanoparticles produced in situ in the pores of said support.

EP 0 672 453 describes palladium-containing catalysts and their preparation for fluid bed vinyl acetate processes.

An advantage of using a palladium-containing catalyst is that any carbon monoxide produced in a prior reaction zone will be consumed in the presence of oxygen and the palladium-containing catalyst in the second reaction zone. An example of a prior reaction zone is a reaction zone for preparing the reactants. This eliminates the need for a separate carbon monoxide removal reactor.

The vinyl acetate reaction may be characterized in terms of conversions based on the reactants. In one embodiment, acetic acid conversions range from 1% to 100%, e.g., from 5% to 50% or from 10% to 45%. Oxygen conversions may range from 1% to 100%, e.g., from 20% to 100% or from 20% to 50%. Ethylene conversions may range from 1% to 90%, e.g., from 5% to 100% or from 10% to 50%. In one embodiment, vinyl acetate selectivity, based on ethylene may range from 20% to 100%, e.g., from 50% to 95% or from 75% to 90%.

In the vinyl acetate reaction, the catalyst may have a productivity (measured in space time yield, STY) ranging from 10 g/hr-liter to 5,000 g/hr-liter, e.g., from 100 g/hr-liter to 2,000 g/hr-liter or from 200 g/hr-liter to 1,000 g/hr-liter, where g/hr-liter means grams of vinyl acetate per hour per liter of catalyst. In terms of upper limits, the space time yield maybe less than 20,000 g/hr-liter, e.g., less than 10,000 g/hr-liter or less than 5,000 g/hr-liter.

Removal of Impurities

Figure 1:
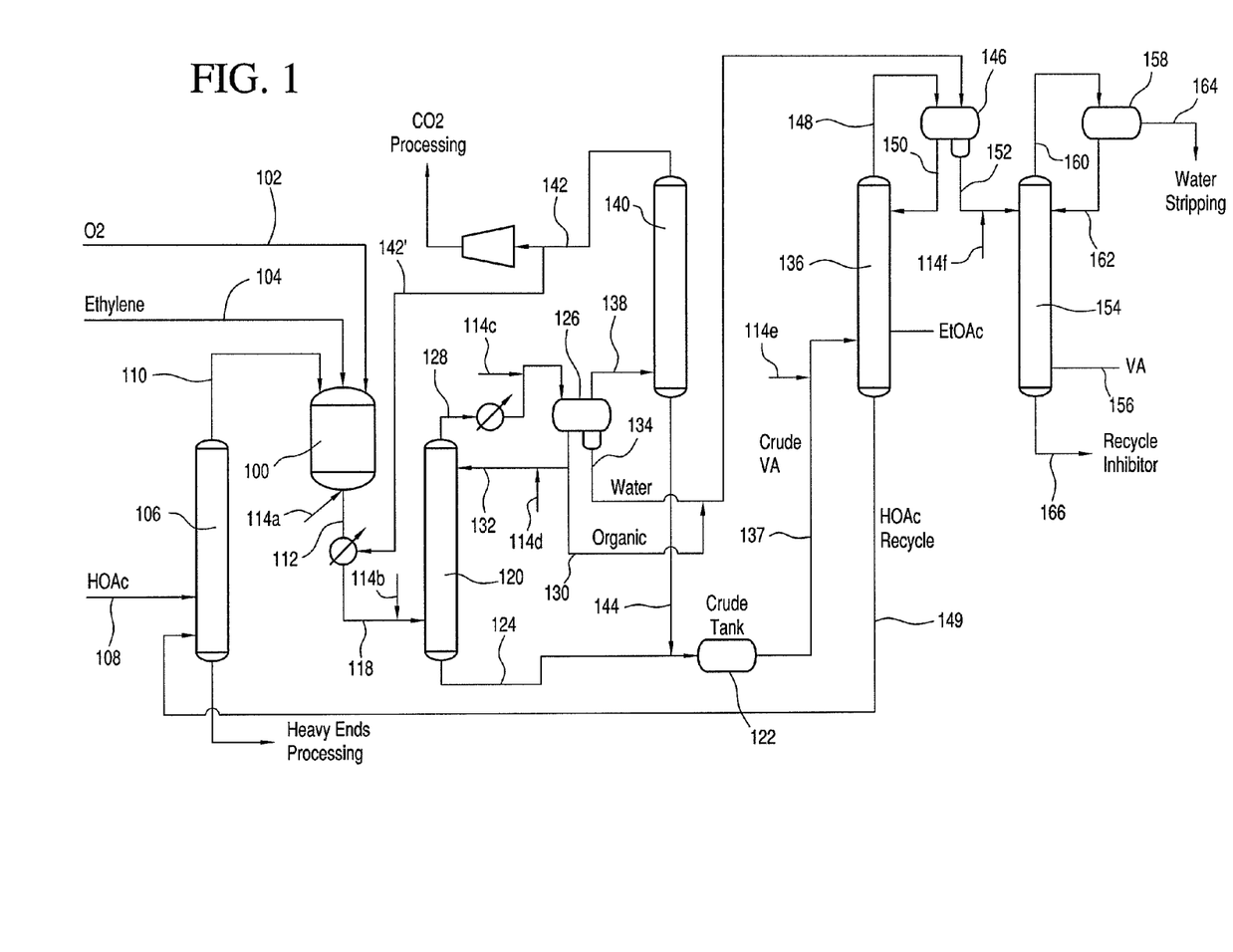
FIG. 1 is a schematic diagram of an exemplary vinyl acetate production process, which includes reaction and separation, for one embodiment of the present invention.

Referring to the embodiments of FIG. 1, oxygen and ethylene are fed to reactor 100 via feed lines 102 and 104, respectively. Optionally, acetic acid is fed to vaporizer 106 via feed stream 108. Vaporized acetic acid exits vaporizer 106 and is directed to reactor 100 via line 110. The vinyl acetate formation reaction takes place in reactor 100. The crude vinyl acetate stream exits reactor 100 via line 112 as an effluent stream.

Preferably, the crude vinyl acetate composition is contacted with at least one scavenger, which inhibits formation of, for example, peroxides, NVR, and/or heavy ends. Regarding inhibition of peroxide formation, without being bound by theory, it is believed that peroxides may be formed from the reaction of oxygen with carbon based radicals. Specifically, peroxides may be formed in equilibrium reactions involving acetic acid, ethylene, oxygen, and/or vinyl acetate. Common peroxide forming compounds include aldehydes and vinyl compounds. It has now been discovered that, these peroxide-forming reactions may occur in the effluent stream that exits the reactor, as well as in the purification units associated with the reactor. It is believed that the scavengers inhibit these equilibrium reactions that form peroxides, thus providing for a reduction in peroxide formation. Peroxides may decompose into oxygen radicals. These oxygen radicals may induce the polymerization of monomers. As a result of the addition of the scavengers, fewer oxygen radicals are formed, monomer polymerization is inhibited, and NVR and heavy ends formation is thus reduced.

Further, with regard to the inhibition of NVR and heavy ends formation, it has now been discovered that a significant amount of oxygen and/or oxygen-containing compounds may be present in a vinyl acetate separation train, e.g., in a PDC. Conventionally, this high oxygen content was not known and, as such, scavengers were not used in these locations. The oxygen and oxygen-containing compounds decompose into oxygen radicals, which, as indicated above, may induce polymerization of monomers, e.g., ethylene or vinyl acetate, or the formation of acetoxyacetic acid from acetic acid and vinyl acetate via an ethylidene diacetate intermediate. As a result, undesired NVR and heavy ends are formed. Conventionally, scavengers have not been utilized as inhibitors of acetoxyacetic acid formation; nor have scavengers been conventionally used to reduce acetoxyacetic acid content. The addition of the scavengers in accordance with the present invention, beneficially inhibits the formation of or reduces the presence of oxygen radicals, which results in inhibition and/or reduction of NVR and/or heavy ends formation.

In some embodiments, the vinyl acetate formation reaction is exothermic and provides for a temperature increase. This temperature increase may induce polymerization of the monomers. This polymerization may be inhibited or reduced by the addition of the scavengers.

In one embodiment, the concentration of oxygen in the mixture of reactants being fed to the reactor may also affect the formation of heavy ends and the inhibition of the formation thereof. As one example, at lower oxygen concentrations, e.g. less than 4% wt. % oxygen, e.g., less than 3 wt. % or less than 2 wt. %, some scavengers, for example parabenzoquinone, may perform better than other scavengers, e.g. hydroquinone. Thus, in one embodiment, when a lower oxygen concentration is utilized in the reaction mixture, parabenzoquinone may be selected as the scavenger. In other embodiments, when a higher oxygen concentration, e.g., greater than 4 wt. %, greater than 5 wt. %, or greater than 7 wt. %, is utilized in the reaction mixture, HQ may be selected as the scavenger package.

As shown in FIG. 1, line 112 may be contacted with one or more scavengers. Line 114a shows one location for a scavenger feed line. Scavenger feed line 114a conveys one or more scavengers to stream 112, thus contacting stream 112 with scavenger(s). One or more, e.g., two or more, lines may be utilized to provide the scavenger(s) to the reactor effluent or to derivative streams of the reactor effluent. Additional exemplary scavenger feed locations are indicated by lines 114b-f. The location of the scavenger feed lines, of course, is not limited to these locations, and additional scavenger lines that provide scavengers to additional derivative streams may be utilized.

Figure 2:
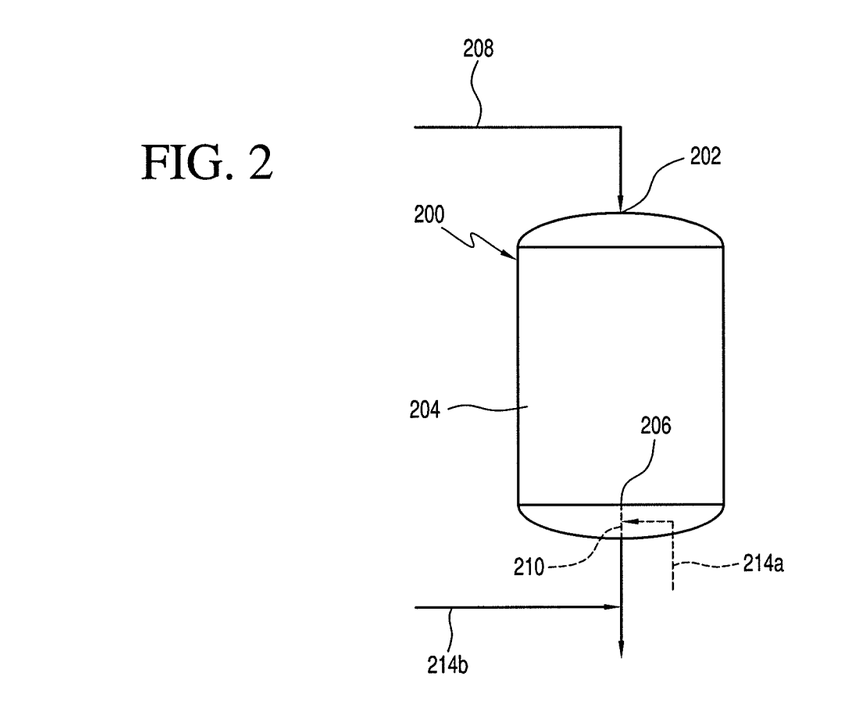
FIG. 2 is a schematic diagram of an exemplary vinyl acetate reactor showing an inlet, a catalyst block portion, and an outlet, for one embodiment of the present invention.

As shown in FIG. 2, reactor 200 comprises inlet 202 for receiving reactants, catalyst block portion 204 for retaining catalyst to catalyze the reaction, and outlet 206 for yielding the crude vinyl acetate composition. Thus, the reactants, e.g., acetic acid, ethylene, and oxygen, enter reactor 200 via line 208. Alternatively, the reactants may enter the reactor separately or in any combination thereof. Line 208 merely represents the collective addition of the reactants to the reactor. The vinyl acetate synthesis reaction occurs in catalyst block portion 204, and the crude vinyl acetate composition, as formed, exits catalyst block portion 204 via stream 210, which directs the crude vinyl acetate composition to and through outlet 206. Outlet 206 is configured downstream of catalyst block portion 204.

In some embodiments, the contacting may occur in outlet 206 of the reactor. For example, scavenger(s) may contact the crude vinyl acetate composition via scavenger feed line 214a. Preferably, the contacting of the crude vinyl acetate composition occurs immediately after catalyst block portion 204 as shown by line 214a and line 214b. "Immediately," in some embodiments, means as the crude vinyl acetate composition exits catalyst block portion 204. In one embodiment, "immediately" means before the crude vinyl acetate composition is conveyed to the purification train. Line 214b illustrates the addition of scavengers immediately after the crude vinyl acetate composition exits reactor 200, e.g., immediately after the reaction of the acetic acid, the oxygen, and the ethylene, but before the purification train.

Although, in preferred embodiments, the scavenger is added to the crude vinyl acetate composition effluent exiting the reactor or to derivatives of the effluent, it is within the contemplation of the invention to add the scavenger at points further upstream thereof. For example, the scavenger may be added to the reactant feed streams, e.g., the oxygen feed, the ethylene feed, and/or the acetic acid feed. Additionally or alternatively, the scavenger may be added directly to the reactor. Addition of scavengers at these points may also inhibit impurity formation in the crude vinyl acetate composition.

The specific composition of the crude vinyl acetate composition may vary widely depending, for example, on the reaction conditions and catalyst employed in addition to the specific scavenger(s) employed. Some exemplary weight percentage ranges for the crude vinyl acetate composition are presented in Table 1.

TABLE 1

Crude Vinyl Acetate Compositions

| Component | Conc. (wt. %) | Conc. (wt. %) | Conc. (wt. %) |
|---|---|---|---|
| Vinyl Acetate | 1 to 75 | 1 to 50 | 2 to 35 |
| Acetic Acid | 1 to 80 | 1 to 50 | 5 to 25 |
| Peroxides | 5 wppm to 25 wppm | 5 wppm to 20 wppm | 10 wppm to 20 wppm |
| Ethylene | 10 to 90 | 10 to 50 | 20 to 40 |
| Ethane | 1 to 40 | 1 to 20 | 5 to 15 |
| Water | 1 to 20 | 1 to 10 | 2 to 8 |
| Carbon Dioxide | 1 to 75 | 1 to 50 | 2 to 35 |

As shown in Table 1, due to the addition of the one or more scavengers, the crude vinyl acetate composition advantageously comprises a low amount of peroxides. This low amount of peroxides may lead to lower amounts of unwanted by-products, e.g., heavy ends, being formed. Because of these low amounts of peroxides and/or resultant by-products, the need for additional separation processes and units to remove same is minimized or eliminated.

Separation

Reverting to FIG. 1, the vinyl acetate production system includes a separation zone to recover and/or purify the vinyl acetate formed in reactor 100. Reactor effluent stream 112 is directed to the separation zone. In one embodiment the separation zone provides at least one derivative of reactor effluent 112. In another embodiment, the derivative stream(s) of the reactor effluent may be any stream that is yielded via the units of the separation zone. Preferably, the derivative streams are downstream of the reactor. Unreacted acetic acid in vapor form may be cooled and condensed. The remainder of the crude vinyl acetate composition in line 118, which is a derivative of the reactor effluent, is directed to PDC 120. In one embodiment, the scavenger is added to line 118 via scavenger feed line 114b. PDC 120 separates the contents of line 118 into a residue comprising vinyl acetate and a distillate comprising vinyl acetate, water, acetic acid, carbon monoxide, carbon dioxide, and ethyl acetate. The vinyl acetate-containing residue is directed to crude tank 122 via line 124. From crude tank 122, the vinyl acetate-containing residue may be stored and/or directed to further processing.

The PDC distillate is optionally cooled, condensed, and directed to an overhead phase separation unit, e.g., decanter 126, via line 128, which is a derivative of the reactor effluent. In preferred embodiments, the scavenger is added to line 128 via scavenger feed line 114c. In one embodiment, the addition of the scavenger occurs in the PDC or downstream thereof. Conditions are desirably maintained in the process such that vapor contents of line 128, once cooled, condensed, and directed to decanter 126, will separate into a light phase and a heavy phase. Scavenger feed line 114c shows addition of the scavenger after the cooling, however, addition prior to cooling is easily within the contemplation of the invention. Generally, line 128 is cooled to a temperature sufficient to condense and separate the condensable components, e.g., vinyl acetate, water, acetic acid, and other carbonyl components, into an aqueous phase and an organic phase. The organic phase exits decanter 126 via line 130. A portion of the organic phase may be refluxed back to PDC 120, as shown by stream 132, which is a derivative of the reactor effluent. In one embodiment, the scavenger is added to line 132 via scavenger feed line 114d. The aqueous phase exits decanter 126 and is directed via line 134 to further separation processing. As an example, line 134 may be directed to decanter 146 of an azeotrope column 136. Lines 130 and 134 optionally may be combined, as shown, and directed to decanter 146 of azeotrope column 136.

Stream 128 may include carbon monoxide, carbon dioxide, ethylene, ethane and other noncondensable gases, which may be directed via stream 138 from decanter 126 to scrubber 140. Scrubber 140 removes, inter alia, carbon monoxide, carbon dioxide, and hydrocarbons such as ethylene and ethane from stream 128. The separated noncondensable components may be conveyed to further processing, e.g., carbon dioxide removal, as shown by stream 142. In another embodiment, at least a portion of stream 142 is recycled back to the reactor effluent or to heat exchange equipment downstream of reactor 100, as shown by stream 142'. The residue exiting scrubber 140 comprises vinyl acetate, water, and acetic acid. The residue is yielded from scrubber 140 via line 144 and may be combined with the vinyl acetate from line 124 prior to being directed to crude tank 122.

From crude tank 122, the vinyl acetate is directed to azeotrope column 136 via line 137, which is a derivative of the reactor effluent. In one embodiment, the scavenger is added to line 137 via scavenger feed line 114e. In another embodiment the addition of the scavenger occurs in azeotrope column 136 or downstream thereof. Azeotrope column 136 separates line 137, which comprises vinyl acetate, acetic acid, and water, into a distillate stream in line 148 and a residue stream 149. Decanter 146 at the top of azeotrope column 136 receives line 134, which comprises the aqueous and organic phases from decanter 126. In addition, decanter 146 receives the distillate from azeotrope column 136. Azeotrope column 136 separates line 137, which comprises vinyl acetate, acetic acid, and water. The residue from azeotrope column 136 comprises acetic acid and water. This stream may be recycled back to vaporizer 106 via line 149, or may be conveyed directly to reactor 100 (not shown). The distillate from azeotrope column 136 comprises vinyl acetate and water and is directed to decanter 146, e.g., a reflux decanter, via line 148. Decanter 146 separates at least a portion of streams 134 and 148 into aqueous and organic phases. The organic phase, which comprises vinyl acetate, exits decanter 146 via line 152, which is a derivative of the reactor effluent, and is directed to further processing. In one embodiment, the scavenger is added to line 152 via scavenger feed line 114f. As one example, line 152 is directed to dehydration column 154. The aqueous phase exits decanter 146 via line 150. Line 150 (or a portion thereof) may be refluxed back to azeotrope column 136.

Dehydration column 154 removes additional water from the contents of line 152, thus yielding purified vinyl acetate via line 156. The water-containing distillate of dehydration column 154 may be directed to overhead tank 158 via line 160. From overhead tank 158, line 162, which contains an amount of vinyl acetate, may be returned to dehydration column 154. Line 164, which comprises water and impurities may be directed to further processing, e.g., water stripping. The residue of dehydration column 154 exits via line 166. The residue comprises various residuals, which may be recycled or otherwise disposed.

Vinyl Acetate Composition

As a result of contacting the crude vinyl acetate composition with one or more scavengers, the treated vinyl acetate composition comprises vinyl acetate and, beneficially, a low amount of impurities, if any. For example, the treated crude vinyl acetate composition may comprise from 1 wt. % to 75 wt. % vinyl acetate, e.g., from 1 wt. % to 50 wt. % or from 2 wt. % to 35 wt. %. Also, the treated crude vinyl acetate composition may comprise at least 5 wt. % vinyl acetate, e.g., at least 10 wt. %, at least 15 wt. %, or at least 20 wt. %. The treated crude vinyl acetate composition may further comprise from 0 wppm to 2,000 wppm impurities, e.g., from 100 wppm to 1,000 wppm or from 250 wppm to 1,000 wppm. In terms of upper limits, the crude vinyl acetate composition may comprise less than 2,000 wppm impurities, e.g., less than 1,000 wppm, less than 500 wppm, less than 250 wppm or less than 100 wppm.

In embodiments where the impurities comprise peroxides, the treated crude vinyl acetate composition comprises from 0 wppm to 10 wppm peroxides, e.g., from 1 wppm to 8 wppm, or from 2 wppm to 7 wppm. In terms of upper limits, the treated crude vinyl acetate composition, in some embodiments, comprises less than 10 wppm peroxides, e.g., less than 8 wppm or less than 7 wppm peroxides.

In embodiments where the impurities comprise NVR and/or heavy ends, the treated crude vinyl acetate composition comprises less than 2,000 wppm NVR and/or heavy ends, e.g., less than 1,000 wppm, less than 500 wppm, less than 250 wppm or less than 100 wppm. In terms of ranges, the treated crude vinyl acetate composition may comprise from 0 wppm to 2,000 wppm NVR and/or heavy ends, e.g., from 100 wppm to 1,000 wppm or from 250 wppm to 1,000 wppm.

Conventionally produced vinyl acetate compositions have not been treated as described herein to remove the impurities, and, as such, contain significantly higher amounts of these impurities. Thus, surprisingly and unexpectedly, the inventive vinyl acetate compositions (either crude or purified) beneficially comprise lower amounts of impurities.

EXAMPLES

The following non-limiting examples describe the various features of the present invention.

Example 1

Approximately 8 wppm of hydrogen peroxide were added to vinyl acetate ("VA")/acetic acid ("HOAc")/water compositions. The VA contained approximately 10 ppm hydroquinone. These compositions represent crude vinyl acetate compositions exiting a vinyl acetate reactor in which peroxide impurities have formed. To this composition were added various levels of scavenger, e.g., ascorbic acid, in the range of 0 to 1010 wppm, as shown in Table 2. This addition of scavenger simulates addition to the crude vinyl acetate composition as this composition exits a reactor. The peroxide levels were then analyzed by the potassium iodide UV-Vis method. The results of these experiments are shown in Table 2.

TABLE 2

Peroxide Reduction with Scavengers

|  | Initial Peroxide Level, wppm | Added Scavenger, wppm | Final Peroxide Level, wppm | % Reduction |
|---|---|---|---|---|
| A (control, no H$_2$O$_2$) | 0 | 0 | 0.000 | — |
| B (control, H$_2$O$_2$ added) | 8.2 | 0 | 8.7 | — |
| Scavenger Package |  |  |  |  |
| 1 | 8.3 | 27.3 | 5.2 | 36.2 |
| 2 | 8.4 | 62.1 | 4.7 | 43.5 |
| 3 | 8.7 | 111.8 | 4.0 | 54.1 |
| 4 | 8.6 | 517.6 | 3.1 | 64.3 |
| 5 | 10.0 | 1010.1 | 0.3 | 97.0 |

As shown in Table 2, the addition of scavenger, in accordance with the present invention, surprisingly and unexpectedly provides for significant reductions in the peroxide level of the resultant vinyl acetate composition. Even at concentrations less than 100 wppm, e.g., Scavengers 1 and 2, the reduction in peroxide level was significant, e.g., greater than 35%.

Example 2

Hydroquinone ("HQ") was added to uninhibited VA/HOAc/water compositions and heated for approximately 5 minutes to 100° C. Examples C and D were compositions that did not utilize an additional scavenger. These compositions represent compositions exiting a vinyl acetate reactor in which little (less than 2 ppm), if any, peroxide impurity has formed. To this composition were added various levels of scavenger, e.g., ascorbic acid, in the range of 0 to 1067 wppm. This addition of scavenger simulates addition to the crude vinyl acetate composition as this composition exits a reactor. The amounts of HQ and ascorbic acid are set forth in Table 3. The peroxide levels were then analyzed by the potassium iodide UV-Vis method. The results of these experiments are shown in Table 3.

TABLE 3

Peroxide Inhibition with Scavengers

|  | Added Scavenger, wppm | Final Peroxide Level, wppm |
|---|---|---|
| C (control, no HQ added) | 0 | 0.148 |
| D (control, HQ added) | 0 | 1.278 |
| Scavenger Package |  |  |
| 6 | 29.6 | 0.704 |
| 7 | 53.37 | 1.352 |
| 8 | 108.3 | 1.167 |
| 9 | 502.1 | 0.111 |
| 10 | 1067.0 | 0.000 |

As shown in Table 3, surprisingly and unexpectedly, the addition of a scavenger in combination with the HQ at levels greater than 500 wppm, in accordance with the present invention, significantly inhibits the formation of peroxides in vinyl acetate compositions.

Example 3

Samples were taken from production lines and comprised VA, HOAc, and water. The samples contained small amounts, if any, parabenzonequinone. These compositions represent crude vinyl acetate compositions exiting a vinyl acetate reactor in which peroxide impurities have formed. To these sample compositions were added approximately 1000 wppm scavenger, as shown in Table 4. The peroxide levels were then analyzed by the potassium iodide UV-Vis method. The results of these experiments are shown in Table 4.

TABLE 4

Peroxide Reduction with Scavengers

|  | Added Scavenger, wppm | Final Peroxide Level, wppm |
|---|---|---|
| E (control) | 0 | 3.704 |
| F (control) | 0 | 3.611 |
| Scavenger Package |  |  |
| 11 | 1176 | 0 |
| 12 | 1036 | 0 |
| 13 | 1059 | 0 |
| 14 | 1036 | 0.481 |

As shown in Table 4, Examples E and F (without scavenger) showed approximately 3.7 wppm peroxides. Surprisingly and unexpectedly, the addition of scavenger to these compositions provides for significant reductions in the peroxide level of the resultant vinyl acetate composition.

Example 4

Samples compositions comprising VA, HOAc, and water were heated for ten minutes at 120° C. To these compositions were added scavengers, as shown in Table 5. A control sample comprising no scavenger was also heated for ten minutes at 120° C. The peroxide levels were then analyzed by the potassium iodide UV-Vis method. The results of these experiments are shown in Table 5. H, I, J, and K represent various scavenger packages that are in accordance with the present invention. The results demonstrate that the combinations of scavengers prevented the formation of some peroxides after heating.

TABLE 5

Peroxide Reduction with Scavengers

|   | Scavenger | Final Peroxide Level, wppm |
|---|---|---|
| G (control) Scavenger Package | 0 | 9.7 |
| 15 | Scavenger H/ Scavenger J | 2.3 |
| 16 | Scavenger I/ Scavenger J | 2.9 |
| 17 | Scavenger H/ Scavenger K | 7.2 |

As shown in Table 5, Examples G (without scavenger) showed approximately 9.7 wppm peroxides. Surprisingly and unexpectedly, the addition of the scavenger packages 15-17 to the VA, HOAc, and water compositions provides for significant reductions in the peroxide level of the resultant vinyl acetate composition.

Example 5

To sample compositions comprising VA, HOAc, and water compositions were added scavengers as shown in Table 6. These samples were heated for ten minutes at 120° C. The peroxide levels were then analyzed by the potassium iodide UV-Vis method. The results of these experiments are shown in Table 6. L and M represent scavenger packages in accordance with the present invention. L represents hydroquinone and M represents a scavenger package comprising multiple scavengers. The results demonstrate that the combination of scavengers prevented the formation of some peroxides after heating.

TABLE 6

Peroxide Reduction with Scavengers

| Scavenger Package | Scavengers, wppm | Final Peroxide Level, wppm |
|---|---|---|
| 18 | 100 wppm Scavenger L | 5.7 |
| 19 | 100 wppm Scavenger M | 4.3 |
| 20 | 50 wppm Scavenger L/ 50 wppm Scavenger M | 3.2 |
| 21 | 25 wppm Scavenger L/ 25 wppm Scavenger M | 3.6 |

As shown in Table 6, the addition of the scavenger packages 18-21 to the VA, HOAc, and water compositions provides for significant reductions in the peroxide level of the resultant vinyl acetate composition. In particular, the combination of Scavenger M and Scavenger L demonstrated synergistic results as compared to the results of the individual components. As shown in Table 6, package 20 showed 44% less final peroxide content than package 18 and 26% less final peroxide content than package 19. Similarly, package 21, which was utilized in only 50 total wppm, showed 37% less final peroxide content than package 18 and 17% less final peroxide content than package 19. The final peroxide amounts for packages 20 and 21 are, surprisingly and unexpectedly, significantly less than the expected amounts The expected amount are based on weighted combinations of the final peroxide values for Scavenger M and Scavenger L. Thus, a synergistic result is demonstrated by packages 20 and 21.

Example 6

Compositions comprising vinyl acetate ("VA"), acetic acid ("HOAc"), and water were prepared at a 30:60:10 weight ratio. These compositions represent compositions exiting a vinyl acetate reactor in which little (less than 2 ppm), if any, NVR/heavy ends have formed. To these compositions were added various levels of scavengers, as shown in Table 7. The compositions were then heated for 10 minutes at 120° C. The heated compositions were then analyzed for NVR/heavy ends content. The results of these experiments are shown in Table 7. N-Q represent various scavengers in accordance with the present invention. N and O represent scavenger packages each comprising multiple scavengers. P represents hydroquinone and Q represents parabenzoquinone.

TABLE 7

Heavy Ends Reduction with Scavengers and/or Peroxides

| Scavenger Package | Added Scavenger | Final NVRHeavy Ends Level, wppm |
|---|---|---|
| Control | — | >2,000 |
| 22 | Scavenger O | 87.5 |
| 23 | Scavenger N | 81.3 |
| 24 | Scavenger P | 47.84 |
| 25 | Scavenger Q | 32.6 |
| 26 | Scavenger O/ Scavenger P | 29.6 |
| 27 | Scavenger N/ Scavenger Q | 11.0 |

As shown in Table 7, the addition of the scavenger packages 22-27 to the VA, HOAc, and water compositions provides for significant reductions in the NVR/heavy ends level of the resultant vinyl acetate composition.

In particular, the combination of Scavenger O with Scavenger P and the combination of Scavenger N with Scavenger Q demonstrated synergistic results as compared to the results of the individual components. As shown in Table 7, package 26 showed 66% less final heavy ends content than package 22, 63% less final heavy ends content than package 23, 38% less heavy ends content than package 24, and 9% less heavy ends content than package 25. Similarly, package 27 showed 88% less final heavy ends content than package 22, 86% less final heavy ends content than package 23, 77% less heavy ends content than package 24 and 68 less heavy ends content than package 25. The final peroxide amounts for packages 26 and 27 are, surprisingly and unexpectedly, significantly less than the expected amounts. The expected amounts are based on weighted combinations of the final heavy ends values for the scavengers. Thus, a synergistic result is demonstrated by packages 26 and 27.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are hereby incorporated by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A method for producing a vinyl acetate composition, the method comprising:
   (a) contacting acetic acid, oxygen, and ethylene under conditions effective to form a crude vinyl acetate stream comprising vinyl acetate, acetic acid, residual oxygen, peroxides, and water;
   (b) contacting the crude vinyl acetate stream or a derivative thereof with at least one scavenger to form a treated crude vinyl acetate composition,
   wherein the at least one scavenger comprises ascorbic acid,
   wherein the contacted crude vinyl acetate composition comprises ascorbic acid present in an amount less than 1067 wppm, based on the total weight of the contacted crude vinyl acetate stream; and
   wherein the treated crude vinyl acetate composition comprises less than 8 wppm peroxides, based on the total weight of the treated crude vinyl acetate composition.

2. The method of claim 1, wherein the treated crude vinyl acetate composition comprises less than 2,000 wppm impurities.

3. The method of claim 2, wherein the impurities comprise non-volatile residues, heavy ends, and/or mixtures thereof.

4. The method of claim 3, wherein the treated crude vinyl acetate composition comprises less than 2,000 wppm heavy ends.

5. The method of claim 1, further comprising separating the crude vinyl acetate composition.

6. The method of claim 5, wherein the separating step comprises separating the treated crude vinyl acetate composition in a first column to form a distillate comprising vinyl acetate, acetic acid, water and impurities and a residue comprising vinyl acetate.

7. The method of claim 6, wherein step (b) occurs in the first column or downstream thereof.

8. The method of claim 6, wherein step (b) occurs in the first column distillate.

9. The method of claim 6, wherein the separating step further comprises separating first column residue in a second column to form a distillate comprising vinyl acetate and water and a residue comprising acetic acid and water.

10. The method of claim 9, wherein step (b) occurs in the second column or downstream thereof.

11. The method of claim 9, wherein step (b) occurs in the second column distillate.

12. The method of claim 9, wherein the separating step further comprises separating the second column residue and/or the second column distillate in at least one additional separation unit.

13. The method of claim 12, wherein step (b) occurs in the at least one additional separation unit or downstream thereof.

14. The method of claim 1, wherein step (a) occurs in a reactor and the reactor comprises an inlet for receiving the reactants, a catalyst block portion for catalyzing a reaction of the acetic acid, the ethylene and the oxygen, and an outlet for exiting the crude vinyl acetate composition.

15. The method of claim 14, wherein step (b) comprises contacting the crude vinyl acetate composition in the outlet.

16. The method of claim 1, wherein the at least one scavenger further comprises is an antioxidant, an inhibitor, or a mixture thereof.

17. The method of claim 1, wherein the acetic acid is produced via a carbonylation method in which the concentration of water maintained in a liquid reaction composition ranges from 0.1 wt. % to 14 wt. %.

18. A method for inhibiting the formation of impurities in an initial crude vinyl acetate stream comprising vinyl acetate, acetic acid, oxygen, peroxides, and water, the method comprising:
   contacting the initial crude vinyl acetate stream or a derivative thereof with at least one scavenger to form a treated crude vinyl acetate composition,
   wherein the at least one scavenger comprises ascorbic acid,
   wherein the contacted crude vinyl acetate composition comprises ascorbic acid present in an amount less than 1067 wppm, based on the total weight of the contacted crude vinyl acetate stream; and
   wherein the treated crude vinyl acetate composition comprises less than 8 wppm peroxides, based on the total weight of the treated crude vinyl acetate composition.

19. The method of claim 18, further comprising separating the initial crude vinyl acetate composition.

20. The method of claim 19, wherein the separating step comprises separating the initial crude vinyl acetate composition in a first column to form a distillate comprising vinyl acetate, acetic acid, water and impurities and a residue comprising vinyl acetate.

21. The method of claim 20, wherein the contacting occurs in the first column or downstream thereof.

22. The method of claim 18, wherein the treated crude vinyl acetate composition comprises less than 2,000 wppm impurities.

23. The method of claim 18, wherein the initial crude vinyl acetate composition comprises the reaction product of acetic acid, oxygen, and ethylene.

24. The method of claim 23, wherein the reaction occurs in a reactor comprising an inlet for receiving reactants, a catalyst block portion for catalyzing the reaction, and an outlet for exiting the initial crude vinyl acetate composition.

25. The method of claim 24, wherein the contacting comprises contacting the initial crude vinyl acetate composition with the at least one scavenger in the outlet of the reactor.

26. A method for reducing peroxide content in a crude vinyl acetate stream comprising vinyl acetate and an initial amount of peroxides, the method comprising:
   contacting the crude vinyl acetate stream or a derivative thereof with at least one scavenger to form a treated vinyl acetate composition comprising vinyl acetate and a reduced amount of peroxides,
   wherein the at least one scavenger comprises ascorbic acid,
   wherein the contacted crude vinyl acetate composition comprises ascorbic acid present in an amount less than 1067 wppm, based on the total weight of the contacted crude vinyl acetate stream.

27. The method of claim 26, wherein the reduced amount is at least 10% less than the initial amount.

* * * * *